United States Patent [19]

Fimuro et al.

[11] Patent Number: 5,245,088
[45] Date of Patent: Sep. 14, 1993

[54] PROCESS FOR CRYSTALLIZING ADDUCT OF BISPHENOL A WITH PHENOL

[75] Inventors: Shigeru Fimuro, Aichi; Akira Yamada; Kenichi Ohmura, both of Kanagawa, all of Japan

[73] Assignee: Mitsui Toatsu Chemicals, Inc., Tokyo, Japan

[21] Appl. No.: 846,996

[22] PCT Filed: Aug. 15, 1991

[86] PCT No.: PCT/JP91/01084
§ 371 Date: Apr. 7, 1992
§ 102(e) Date: Apr. 7, 1992

[87] PCT Pub. No.: WO92/03400
PCT Pub. Date: Mar. 5, 1992

[30] Foreign Application Priority Data
Aug. 21, 1990 [JP] Japan .................... 2-218115

[51] Int. Cl.⁵ .................... C07C 37/84; C07C 39/12
[52] U.S. Cl. .................... 568/724; 568/722
[58] Field of Search ............. 568/722, 723, 724, 727

[56] References Cited
U.S. PATENT DOCUMENTS
4,950,805  8/1990  Iimuro et al. .......... 568/724
4,950,806  8/1990  Iimuro et al. .......... 568/724
4,954,661  9/1990  Iimuro et al. .......... 568/727

FOREIGN PATENT DOCUMENTS
0687780   6/1964   Canada .............. 568/724
63-26735  5/1988   Japan .
1-213246  8/1989   Japan .
1-316335 12/1989   Japan .

*Primary Examiner*—Werren B. Lone
*Attorney, Agent, or Firm*—Burns, Doane, Swecker & Mathis

[57] ABSTRACT

A process for preparing high-purity bisphenol A by estimating on line slurry concentration of a bisphenol A-phenol adduct in a crystallizer on the basis of a material balance and a heat balance around the crystallizer and thereby maintaining said slurry concentration at a prescribed level to precipitate the crystals of said adduct. The slurry having a constant concentration can be always fed to a slurry separating step, thereby enabling steady operation of the slurry separating step. Thus, the process is useful for enhancing productivity. As a result, extraordinary adhesion of the impurity-containing filtrate to the crystals of the bisphenol A-phenol adduct can be inhibited in the slurry separating step, and hence high-purity bisphenol A can be obtained.

1 Claim, 2 Drawing Sheets

PROCESS FOR CRYSTALLIZING ADDUCT OF BISPHENOL A WITH PHENOL

BACKGROUND OF THE INVENTION

1. Field of the Invention

The present invention relates to a process for continuously crystallizing a high purity adduct of bisphenol A with phenol.

More particularly, the invention relates to a process for continuously crystallizing the high purity adduct of bisphenol A with phenol from a slurry having the highest concentration which can continuously separate the adduct crystal and filtrate from the slurry by controlling the amount fed to a crystallizer with a computer.

2. Description of the Related Art

There has recently been an increased demand for bisphenol A as a material for engineering plastics in addition to a material for polycarbonate resin and epoxy resin. Colorless and high purity bisphenol A is required for these uses.

In a process for preparing the high purity bisphenol A, for example, phenol is reacted with acetone in the presence of an acid catalyst, and the reaction product is treated to remove the catalyst, water and a small amount of phenol. The residual liquid mixture is cooled to crystallize bisphenol A in the form of an adduct with phenol, precipitated adduct crystals are separated from the mother liquor, and phenol is removed from the adduct to recover bisphenol A.

The process of preparing high purity bisphenol A by crystallizing the adduct of bisphenol A with phenol (hereinafter referred to as bisphenol A-phenol adduct) has been disclosed, for example, in Japanese Patent Publication SHO 63-26735(1988). That is, a phenol solution of bisphenol A which was prepared in the presence of a hydrochloric acid catalyst is cooled to a range of 35° to 70° C. while feeding 2 to 20% by weight of water to the solution under reduced pressure, precipitated crystals of bisphenol A-phenol adduct are filtered to separate the crystals, and phenol is evaporated from the crystals to obtain high purity bisphenol A.

The process is characterized in that by-products and impurities are separated from bisphenol A by precipitating the bisphenol A-phenol adduct.

Precipitation of the adduct can be controlled by adjusting the amount of feed water so as to maintain a constant temperature under reduced pressure. However, in the process, a rapid increase in the concentration of bisphenol A in the phenol solution leads to a rapid increase in the concentration of the crystallized adduct in the slurry and causes problems such as blocking of the liquid transfer line to a slurry separation step.

Japanese Laid Open Patent HEI 1-213246(1989) discloses a process for crystallizing bisphenol A-phenol adduct from a phenol solution of bisphenol A wherein the concentration of bisphenol A in the solution is controlled by removing a portion of bisphenol A in the solution or by addition of phenol to the solution according to feed-back control on the basis of density measurement of the solution.

Further, Japanese Laid-Open Patent HEI 1-316335(1989) discloses a process for crystallizing bisphenol A-phenol adduct which is characterized by maintaining the temperature of the internal surface of the crystallizer at 5° C. or less higher than the temperature of the reaction mixture in order to obtain the bisphenol A-phenol adduct in a high purity.

These methods are effective as long as the process is steadily carried out. However, the former cannot follow a rapid change of conditions and the latter does not disclose a practical procedure for controlling the crystallization.

A difficult and important technique to precipitate the crystals of bisphenol A-phenol adduct from a liquid mixture of bisphenol A and phenol is to detect operation conditions of the crystallization system which are always varying by disturbance and to maintain the concentration of the adduct in the slurry (hereinafter referred to as slurry concentration) at a constant level. As a practical problem for example, when the slurry concentration of the adduct rises above the desired level in the crystallizer, impurity containing filtrate attaches, to the crystal of bisphenol A-phenol adduct in the slurry separation step, or an increased amount of impurity is included into the crystal of the bisphenol A-phenol adduct, and hence purity and hue of the product bisphenol A are seriously damaged.

Further, too high a slurry concentration in the course of transferring the adduct slurry from the crystallizer to the slurry separation step leads to problems such as blocking of transfer piping in a short period and abrasion leaks or clogging of a pump in a medium or long period, and further causes troubles of the slurry separator itself. Thus, too high slurry concentration seriously impairs productivity and in the worst case, operation of the whole production system must be stopped.

On the other hand, when the slurry concentration of the crystallizer is set at a low level in order to avoid the above problems, the rate of crystallization remarkably decreases and scale up of crystallizer volume becomes necessary. Further, equipment for treating a large amount of filtrate is needed and thus efficiency of the whole production facility is severely decreased.

In order to solve these problems, it is important to prescribe a desired value for a slurry concentration and to carry out a rapid and accurate control of the slurry concentration. In order to accurately control the slurry concentration in the crystallizer, ever changing slurry concentration must be immediately checked. However, the slurry concentration depends upon a complex material balance and heat balance among the three phases of vapor, liquid and solid in the crystallizer, and is hence very difficult to manage and control.

The slurry concentration of the bisphenol A-phenol adduct becomes higher at a lower temperature and at a lower concentration of water. However, an increased amount of feed water to the crystallizer under reduced pressure leads to an increase in the slurry concentration due to the decrease in temperature caused by the latent heat of water evaporation, and contrary results occur when the slurry concentration is reduced by an increased amount of water due to non-evaporation of water. Thus, variation of the slurry concentration is difficultly detected due to the presence of both effects. Further, the system is complex because each phenomenon varies depending upon the concentration of bisphenol A and temperature of the solution. Therefore, rapid and accurate control of the slurry concentration is very difficult.

Accordingly, one object of the present invention is to provide a process for crystallizing a high purity bisphenol A-phenol adduct from the solution of bisphenol A in phenol without the above problems.

SUMMARY OF THE INVENTION

The present inventors have carried out an intensive investigation on the precipitation of the bisphenol A-phenol adduct in the crystallizer in order to accomplish the above object. As a result, they have found that the above object can be achieved by estimating on line the slurry concentration of the bisphenol A-phenol adduct in the crystallizer with a computer, comparing the estimate with a prescribed, desired value and automatically controlling the amount of feed water so that the estimate of the slurry concentration maintains the desired value. Thus the present invention has been completed.

That is, one aspect of the invention is a crystallization process of bisphenol A-phenol adduct with a system comprising a line for feeding a raw material of crystallization, means for changing internal temperature, internal pressure and jacket temperature of a crystallizer, a line for feeding water to the crystallizer and means for discharging and separating the crystals of bisphenol A-phenol adduct formed in the crystallizer, comprising the steps of inputting to a computer information on (1) a composition of the raw material to be fed to the crystallizer and of water or of an aqueous solution containing a small amount of phenol, inputting to the computer through a detector and a signal circuit which are mounted on the system an information on (2) temperature and flow rate of the raw material in the course of feeding to the crystallizer, (3) temperature and pressure in the crystallizer, (4) jacket temperature of the crystallizer, and (5) flow rate and temperature of water in the course of feeding to the crystallizer, operating and estimating a composition in the crystallizer and a slurry concentration of bisphenol A-phenol adduct through a calculating mechanism of the computer, comparing the estimate of the slurry concentration with a prescribed set point, controlling the amount of water fed to the crystallizer, and thereby maintaining the slurry concentration of the bisphenol A-phenol adduct at a prescribed level.

According to the process of the invention, the slurry concentration of the bisphenol A -phenol adduct in the crystallizer can be controlled within a specified range.

As a result, the slurry having a constant concentration can be always fed to a slurry separating step, thereby enabling steady operation of the slurry separating step. Thus, the process is useful for enhancing productivity.

Further, extraordinary adhesion of the impurity-containing filtrate to the crystal of the bisphenol A-phenol adduct can be inhibited in the slurry separating step, and hence high-purity bisphenol A can be obtained.

BRIEF DESCRIPTION OF THE DRAWINGS

In FIG. 1 and FIG. 2, symbols are defined as follows.
1. Computer
2. Crystallizer
3. Condenser
4. Liquid solid separator for slurry
5. Pump
11. Water feed line
12. Bisphenol A-phenol solution feed line
13. Phenol-steam line
14. Uncondensed gas line
15. Condensed liquid line
16. Slurry line
17. Separated adduct crystal line
18. Separated filtrate line
19. Water flowmeter
20. Water thermometer
21. Crystallization material flowmeter
22. Crystallization material thermometer
23. Interior crystallizer thermometer
24. Interior crystallizer pressure gauge
25. Crystallizer operating pressure gauge
26. Crystallizer jacket thermometer
11C. Valve
$C_s$. Slurry concentration in crystallizer
$C_s^s$. Set point of slurry concentration
$F_w$. Amount of water added

PREFERRED EMBODIMENTS OF THE INVENTION

The control system for use in the process of the invention is a system for crystallizing the bisphenol A-phenol adduct and separating the crystallized adduct, which comprises a line for feeding the raw material of crystallization, means for operating the internal temperature and pressure and jacket temperature of the crystallizer, a line for feeding water to the crystallizer, and means for discharging and separating the bisphenol A-phenol adduct which was crystallized in the crystallizer.

Figure 1:
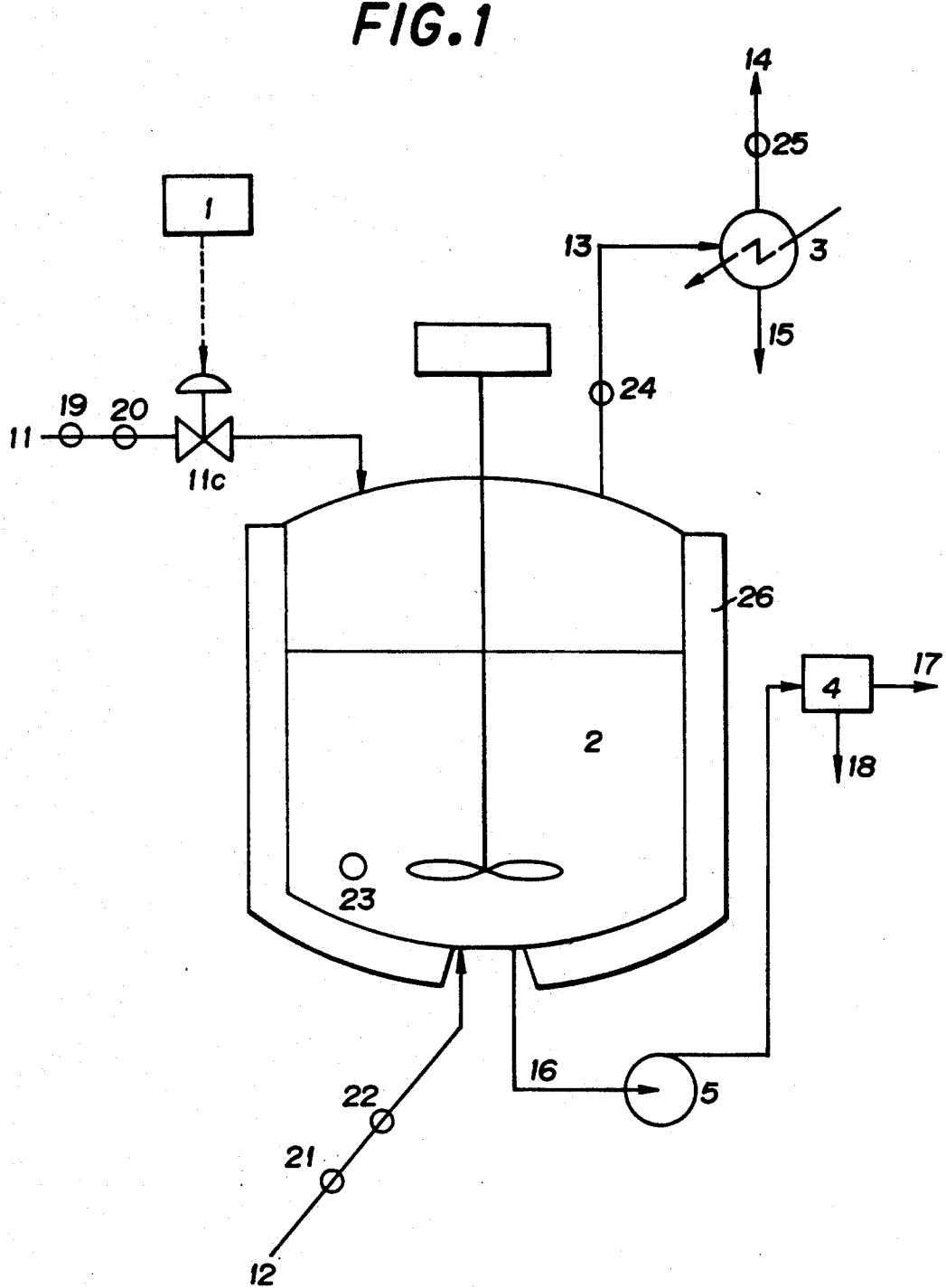
FIG. 1 is an example illustrating a process flow diagram for conducting the process of the present invention.

FIG. 1 exemplifies a practical process flow diagram of the system. In the drawing, the raw material for crystallization, i.e., impurity-containing liquid mixture of bisphenol A and phenol is fed through the line 12, and cooling water or water containing a small amount of phenol is fed through the line 11, respectively, to the continuous crystallizer 2. The continuous crystallizer 2 is maintained under reduced pressure of 20 to 100 mg Hg by vacuum equipment through lines 13 and 14, and thus the interior temperature of the crystallizer is lowered to 35° to 70° C. due to evaporation of phenol-containing water. As a result, crystals of the bisphenol A-phenol adduct precipitate in the crystallizer. Steam evaporated through the line 13 and containing a small amount of phenol is wholly condensed by the condenser 3. Condensed liquid is discharged from the line 15 and uncondensed gas is discharged from the line 14, respectively. On the other hand, the slurry of the bisphenol A-phenol adduct is fed through the line 16 by the pump 15 to the slurry separator 4. The crystals of the bisphenol A-phenol adduct are separated through the line 17 and the filtrate is separated through the line 18, respectively.

The process of the invention applies a computer to the above system, using as a manipulated variable the opening of the value 11C in the water feed line 4, controlling the amount of water to be fed to the crystallizer, and thereby controlling the slurry concentration of the crystals of the bisphenol A-phenol adduct in the crystallizer. Consequently, the system is constituted in combination with a computer. That is, in FIG. 1, the computer is fed the following data (1) the composition of the raw material to be fed to the crystallizer and the composition of water or phenol-containing water which are separately operated, and is input through a detector and a signal circuit, (2) dispatch signals on the temperature 21 and flow rate 22 of the raw material in the course of feeding to the crystallizer, (3) dispatch signals on the internal temperature 23 and pressure 24 and 25 of the crystallizer, (4) a dispatch signal on the jacket temperature 26 of the crystallizer, and (5) dispatch signals on the flow rate 19 and temperature 20 of the water in the course of feeding to the crystallizer. The computer thereby operates a composition in the crystallizer and a slurry concentration of the bisphenol A-phenol adduct to obtain estimates of the same, compares the estimates with a prescribed set point, determines the amount of water to be fed to the crystallizer so as to maintain the slurry concentration of the bisphenol A-phenol adduct at a specified value, and outputs a directive signal so as to maintain the slurry concentration of the bisphenol A-phenol adduct at the specified value by operating the opening of the value 11c and controlling the amount of water in the course of feeding to the crystallizer.

The slurry concentration of the crystals of the bisphenol A-phenol adduct in the crystallizer is estimated by applying the computer and operating various data which are input on line. The slurry concentration is maintained in a range of the desired value so as to avoid troubles in the next slurry separation step. Practically, the slurry concentration of the bisphenol A-phenol adduct is preferably controlled to be in the range of 35 to 50% by weight.

The process of the present invention is a process for continuously crystallizing the bisphenol A-phenol adduct from the phenol solution of bisphenol A in the crystallizer, which is most characterized, with an application of the computer as mentioned above, by estimating the slurry concentration of the bisphenol A-phenol adduct in the crystallizer and setting the estimates to the desired value of the control system.

For example, a slurry concentration is set to a desired value in the process of crystallizing the bisphenol A-phenol adduct from a phenol solution of bisphenol A. In the case of environmental change or disturbance such as a rapid increase in the concentration of the raw material for crystallization, i.e., the phenol solution of impurity-containing bisphenol A, adjustment of the amount of feed water so as to maintain a constant crystallization temperature as a control value often increases slurry concentration. Further, when the amount of feed water is increased by setting the slurry concentration to a control amount for adjusting the amount of water, it is anticipated to lower the temperature by increasing evaporation of water and to increase up the slurry concentration. On the other hand, an increase in the amount of water leads to an increase in the amount of unevaporated water and lowers the slurry concentration, which is an opposite effect. These effects differ depending upon the concentration level of bisphenol A and crystallizing temperature, and are difficult to judge unless estimated with the computer.

Conventionally, the slurry concentration has been impossible to directly measure with a sensor under the constantly changing environment of the crystallization system by the influence of disturbances. The present invention, however, estimates the slurry concentration in real time on line by operating with a model on the basis of a solubility equation.

Figure 2:
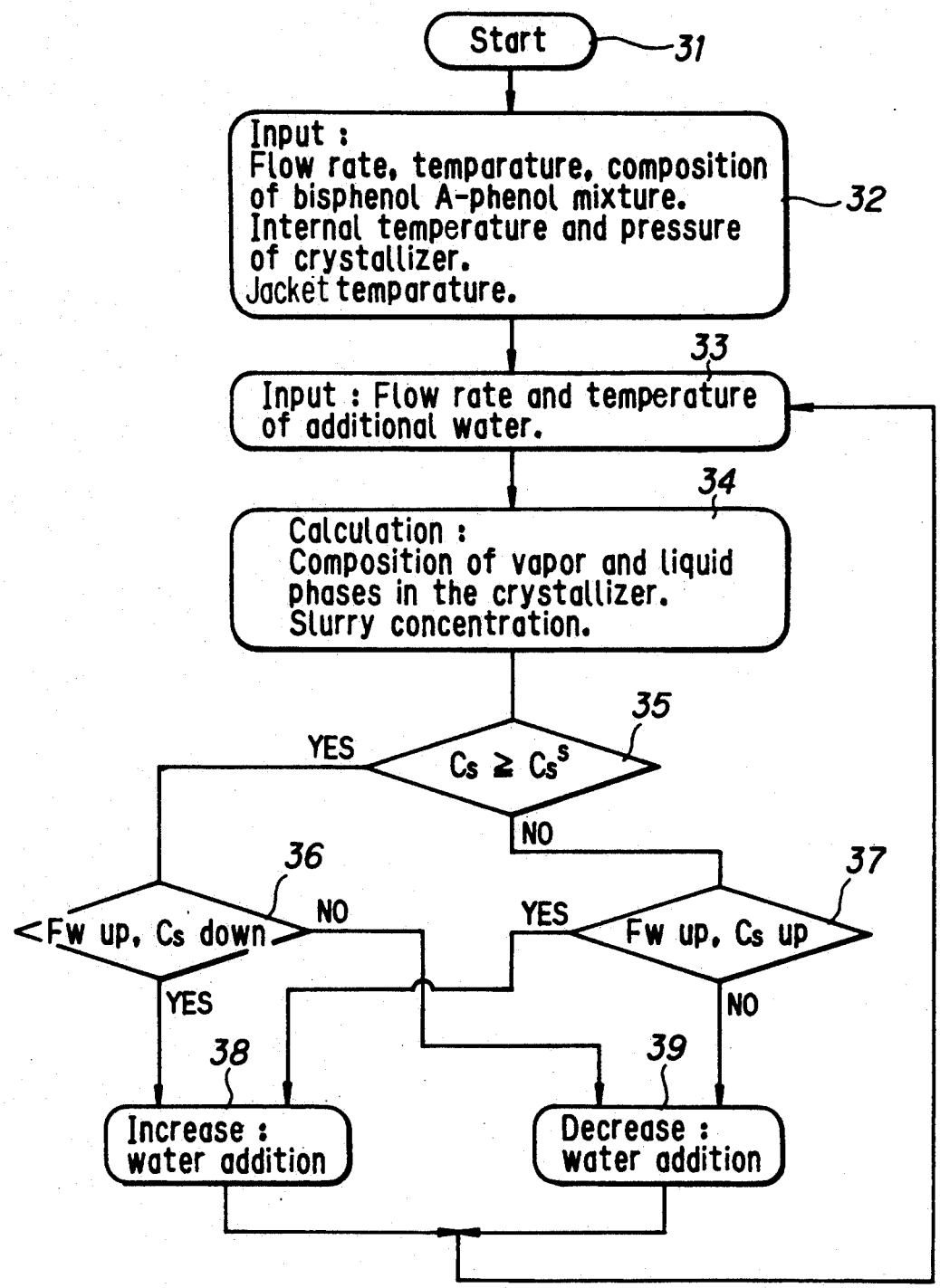
FIG. 2 is a flow chart illustrating control procedures in the reactor of FIG. 1.

Practical control procedures will be illustrated by the block flow diagram of FIG. 2 which shows the controlling procedures of the invention.

The flow rate and temperature of the crystallization material consisting of the phenol solution of bisphenol A which is fed through the line 12 are input as dispatch signals from the flow meter 21 and thermometer 22 which are fitted on the line 12, the temperature and pressure in the interior of the crystallizer are input as dispatch signals from the thermometer 23 and pressure gauge 24 which are equipped on the crystallizer, and the jacket temperature of the crystallizer is input as a dispatch signal from the thermometer 26 which is fitted on the jacket, respectively, to the computer 1 (Step 32). The temperature and flow rate of water or water containing a small amount of phenol which is fed through the line 11 are input to the computer 1 as dispatch signals from the flow meter 19 and thermometer 20 (Step 33). Further, the composition of crystallization material consisting of the phenol solution of bisphenol A which is fed through the line 12 and a composition of water or water containing a small amount of phenol are separately operated with a computer and thus-obtained values are input to the computer 1. On the basis of the input information, the material balance and heat balance are operated in real time to estimate the gas phase composition, liquid phase composition and the slurry concentration in the interior of the crystallizer (Step 34).

In carrying out the above operation, the estimates obtained by separately operating various experimental data on the liquid-solid equilibrium in the crystallization of the bisphenol A-phenol adduct and of each component are built in the logic of the computer 1. The slurry concentration Cs which is estimated by the computer 1 is compared with the desired value $Cs^s$ (Step 35). The added amount of water Fw is adjusted so as to maintain the desired value (set point) $Cs^s$ (Steps 38 and 39).

Practical control procedures as follows. When the estimated slurry concentration Cs is not lower than the desired value $Cs^s$, i.e., the step 35 is YES, opening of the value 11c is adjusted by the output of the computer 1, and the amount of added water Fw is increased. When the slurry concentration Cs is decreased, i.e., the step 36 is YES, the amount of added water Fw is similarly increased by the computer 1 (Step 38). On the contrary, when the slurry concentration Cs is increased, i.e., the step 36 is NO, the amount of added water is decreased (Step 39). Further, the estimated slurry concentration Cs is lower than the desired value $Cs^s$, i.e., the step 35 is NO, opening of the valve 11c is adjusted by the output signal of the computer 1, and the amount of added water Fw is increased. When the slurry concentration is increased, i.e., the step 37 is YES, the amount of added water Fw is similarly increased by the computer 1 (Step 38). On the contrary, the slurry concentration is decreased, i.e., the step 37 is NO, the amount of added water Fw is decreased (Step 39).

The above loop composed of the steps 33 to 39 is recycled with a cycle of from a few seconds to several dozens of minutes. The slurry concentration Cs in the crystallizer is controlled to always maintain the desired value $Cs^s$.

In such a case, crystallization step can be composed of multiple crystallizers. The slurry concentration in each crystallizer is estimated and more accurate control can be effectively carried out by adjusting the amount of feed water to each crystallizer.

EXAMPLE

The present invention will hereinafter be illustrated further in detail by way of examples. In the examples, percent means percent by weight unless otherwise noted.

EXAMPLE 1

Phenol and acetone were mixed and hydrogen chloride was continuously blown through the mixture. The condensation reaction was carried out at 55° C. for 8 hours. The reaction mixture was heated at reduced pressure to remove hydrogen chloride and water which was generated by the reaction. The resulting liquid was a phenol solution of crude bisphenol A and had a following composition.

| | |
|---|---|
| Bisphenol A | 30.0% |
| o,p'-Isomer | 0.8% |
| Other impurities | 1.0% |
| Phenol | 68.2% |

The phenol solution of bisphenol A was transferred to a crystallizer operating at a temperature of 90° C., pressure of 50 mm Hg and a flow rate of 400 kg/hr.

The data were input on line to a computer at 10 second intervals on the flow rate and temperature of the phenol solution, the flow rate and temperature of water fed through a separate line, and the level and pressure of the crystallizer. Thus the slurry concentration in the crystallizer was estimated and water was added to the reactor so as to obtain a constant slurry concentration of about 40%. Balance was obtained at a water flow rate of about 30 kg/hr. The interior temperature of the crystallizer was about 55° C.

In the next step, a phenol solution containing 35.0% of bisphenol A was transfered to the crystallizer. As a result, the slurry concentration was controlled to about 40% and finally a water flow rate of about 33 kg/hr and temperature of about 55° C. in the crystallizer.

The volume of the phenol solution containing bisphenol A in the crystallizer was separately controlled so as to obtain an average residence time of 2 hours. The slurry was continuously discharged from the crystallizer and filtered.

COMPARATIVE EXAMPLE 1

A phenol solution of crude bisphenol A was prepared by the same procedures as described in Example 1. The phenol solution was transferred to a crystallizer operating at a temperature of 90° C., pressure of 50 mm Hg, and flow rate of 400 kg/hr. Feed back control was carried out so as to maintain the interior temperature of the crystallizer at about 55° C. and water was added to the crystallizer. Balance was obtained at a water flow rate of about 30 kg/hr and slurry concentration of about 40%.

In the next step, a phenol solution containing 35.0% of bisphenol A was transfered to the crystallizer. As a result, the interior temperature of the crystallizer was controlled to about 55° C. The water flow rate was finally about 35 kg/hr and slurry concentration was about 45% while the slurry was continuously discharged from the crystallizer at a flow rate of 150 kg/hr and filtered. However, the discharge line became clogged and discharge became impossible. The volume of the phenol solution in the crystallizer was separately controlled to obtain an average residence time of 2 hours.

Industrial Applicability

In a process for preparing bisphenol A by reaction of phenol with acetone, adduct of bisphenol A and phenol can be continuously crystallized in high purity by controlling the crystallization step with a computer.

Colorless and high purity bisphenol A is required in the field of resin using bisphenol A as a raw material and thus the process of the present invention is very valuable.

We claim:

1. A continuous crystallization process for a high purity bisphenol A-phenol adduct with a system comprising a line for feeding a raw material of crystallization, means for changing internal temperature, internal pressure and jacket temperature of a crystallizer, a line for feeding water to the crystallizer and means for discharging and separating the crystals of bisphenol A-phenol adduct formed in the crystallizer, said process comprising the steps of inputting to a computer information on (1) composition of the raw material to be fed to the crystallizer and composition of water or an aqueous solution containing a small amount of phenol, inputting to the computer through a detector and a signal circuit which are mounted on the system information on (2) temperature and flow rate of the raw material in the course of feeding to the crystallizer, (3) temperature and pressure in the crystallizer, (4) jacket temperature of the crystallizer, and (5) flow rate and temperature of water in the course of feeding to the crystallizer, operating and estimating a composition in the crystallizer and a slurry concentration of bisphenol A-phenol adduct through a calculating mechanism of the computer, comparing the estimate of the slurry concentration with a prescribed set point, controlling an amount of water fed to the crystallizer, and thereby maintaining the slurry concentration of the bisphenol A-phenol adduct from 35 to 50 percent by weight at a temperature of from 35° to 75° C., and a pressure of from 20 to 100 mm Hg.

* * * * *

UNITED STATES PATENT AND TRADEMARK OFFICE
CERTIFICATE OF CORRECTION

PATENT NO. : 5,245,088
DATED : September 14, 1993
INVENTOR(S) : Shigeru IIMURO et al It is certified that error appears in the above-indentified patent and that said Letters Patent is hereby corrected as shown below:

On the title page, Item [75] Inventors: "Fimuro" should read --Iimuro--

Column 1, line 18, "Been" should read --been--.

In the Drawings:
In Figure 2, frame 32, "temparature" should read --temperature--.

Signed and Sealed this

Thirty-first Day of May, 1994

Attest:

BRUCE LEHMAN

Attesting Officer     Commissioner of Patents and Trademarks